United States Patent
Karavani et al.

Patent Number: 6,123,691
Date of Patent: Sep. 26, 2000

[54] FEMALE URINATING AID

[76] Inventors: David Karavani; Ronen Ramot, both of 2178 Tally Ho Ave., Las Vegas, Nev. 89119

[21] Appl. No.: 09/262,203

[22] Filed: Mar. 4, 1999

[51] Int. Cl.⁷ .................................................. A61F 5/44
[52] U.S. Cl. ............................................................ 604/329
[58] Field of Search ................................ 604/327, 328, 604/329, 330, 331, 346, 347, 349, 264, 523

[56] References Cited

U.S. PATENT DOCUMENTS

| | | | |
|---|---|---|---|
| 4,626,250 | 12/1986 | Schneider | 604/352 |
| 4,681,572 | 7/1987 | Tokarz et al. | 604/329 |
| 4,713,066 | 12/1987 | Komis | 604/353 |
| 4,784,655 | 11/1988 | Campion et al. | 604/349 |
| 4,846,816 | 7/1989 | Manfredi | 604/323 |
| 4,889,532 | 12/1989 | Metz et al. | 604/330 |
| 5,053,027 | 10/1991 | Manfredi | 604/327 |
| 5,205,298 | 4/1993 | Hurst | 128/844 |

*Primary Examiner*—Wynn Wood Coggins
*Assistant Examiner*—Deborah Blyveis

[57] ABSTRACT

A female urinating aid for permitting a female user to direct the flow of urine therefrom. The female urinating aid includes a bendable corrugated tube with a pair of opposite open ends. A disk-shaped shield outwardly radiates about the tube and is located towards and spaced apart a first end of the tube.

7 Claims, 2 Drawing Sheets

FEMALE URINATING AID

BACKGROUND OF THE INVENTION

1. Field of the Invention

The present invention relates to female urinating aids and more particularly pertains to a new female urinating aid for permitting a female user to direct the flow of urine therefrom.

2. Description of the Prior Art

The use of female urinating aids is known in the prior art. More specifically, female urinating aids heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,583,983; U.S. Pat. No. 4,986,823; U.S. Pat. No. 5,370,637; U.S. Pat. No. 3,072,125; U.S. Pat. No. 3,556,102; and U.S. Pat. No. Des. 363,987.

While these devices fulfill their respective, particular objectives and requirements, the aforementioned patents do not disclose a new female urinating aid. The inventive device includes a bendable corrugated tube with a pair of opposite open ends. A disk-shaped shield outwardly radiates about the tube and is located towards and spaced apart a first end of the tube.

In these respects, the female urinating aid according to the present invention substantially departs from the conventional concepts and designs of the prior art, and in so doing provides an apparatus primarily developed for the purpose of permitting a female user to direct the flow of urine therefrom.

SUMMARY OF THE INVENTION

In view of the foregoing disadvantages inherent in the known types of female urinating aids now present in the prior art, the present invention provides a new female urinating aid construction wherein the same can be utilized for permitting a female user to direct the flow of urine therefrom.

The general purpose of the present invention, which will be described subsequently in greater detail, is to provide a new female urinating aid apparatus and method which has many of the advantages of the female urinating aids mentioned heretofore and many novel features that result in a new female urinating aid which is not anticipated, rendered obvious, suggested, or even implied by any of the prior art female urinating aids, either alone or in any combination thereof.

To attain this, the present invention generally comprises a bendable corrugated tube with a pair of opposite open ends. A disk-shaped shield outwardly radiates about the tube and is located towards and spaced apart a first end of the tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new female urinating aid apparatus and method which has many of the advantages of the female urinating aids mentioned heretofore and many novel features that result in a new female urinating aid which is not anticipated, rendered obvious, suggested, or even implied by any of the prior art female urinating aids, either alone or in any combination thereof.

It is another object of the present invention to provide a new female urinating aid which may be easily and efficiently manufactured and marketed.

It is a further object of the present invention to provide a new female urinating aid which is of a durable and reliable construction.

An even further object of the present invention is to provide a new female urinating aid which is susceptible of a low cost of manufacture with regard to both materials and labor, and which accordingly is then susceptible of low prices of sale to the consuming public, thereby making such female urinating aid economically available to the buying public.

Still yet another object of the present invention is to provide a new female urinating aid which provides in the apparatuses and methods of the prior art some of the advantages thereof, while simultaneously overcoming some of the disadvantages normally associated therewith.

Still another object of the present invention is to provide a new female urinating aid for permitting a female user to direct the flow of urine therefrom.

Yet another object of the present invention is to provide a new female urinating aid which includes a bendable corrugated tube with a pair of opposite open ends. A disk-shaped shield outwardly radiates about the tube and is located towards and spaced apart a first end of the tube.

Still yet another object of the present invention is to provide a new female urinating aid that lets a female user urinate while stranding upright so that the user does not have to sit or squat down to urinate which is especially useful when trying to avoid sitting on a dirty toilet seat.

Even still another object of the present invention is to provide a new female urinating aid that allows a female user to into urinate a urinal.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
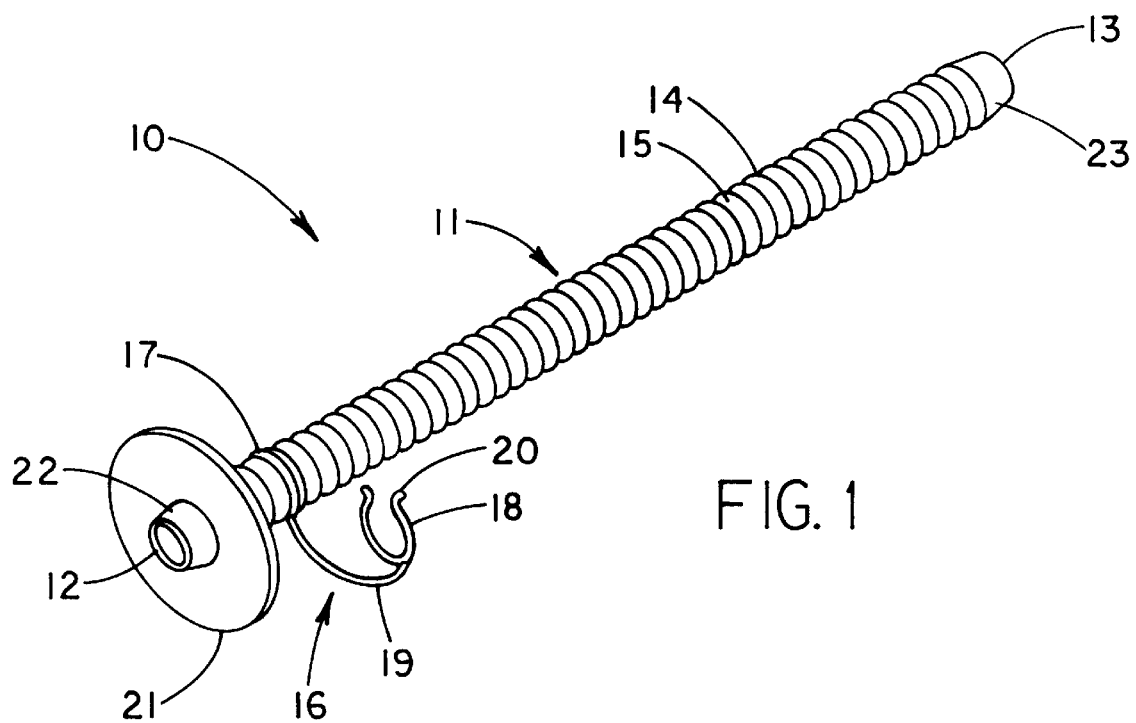
FIG. 1 is a schematic perspective view of a new female urinating aid in an extended position.

With reference now to the drawings, and in particular to FIGS. 1 through 4 thereof, a new female urinating aid embodying the principles and concepts of the present invention and generally designated by the reference numeral 10 will be described.

As best illustrated in FIGS. 1 through 4, the female urinating aid 10 generally comprises a bendable corrugated tube with a pair of opposite open ends. A disk-shaped shield outwardly radiates about the tube and is located towards and spaced apart a first end of the tube.

In closer detail, the female urinating aid 10 comprises an elongate tube 11 has a pair of opposite open ends 12,13, and a longitudinal axis extending between the ends of the tube. The tube comprises a bendable corrugated tube having a series of alternating annular constricted and bellowed portions 14,15 forming a plurality of annular pleats extending in a row extending between the ends of the tube. Each of the bellowed portions 15 of the tube has an outermost diameter defined substantially perpendicular to the longitudinal axis of the tube. Preferably, the outermost diameters of the bellowed portions are about equal to one another so that an outer diameter of the tube defined by the outermost diameters of the bellowed portions is generally constant along the longitudinal axis of the tube between the ends of the tube.

Figure 2:
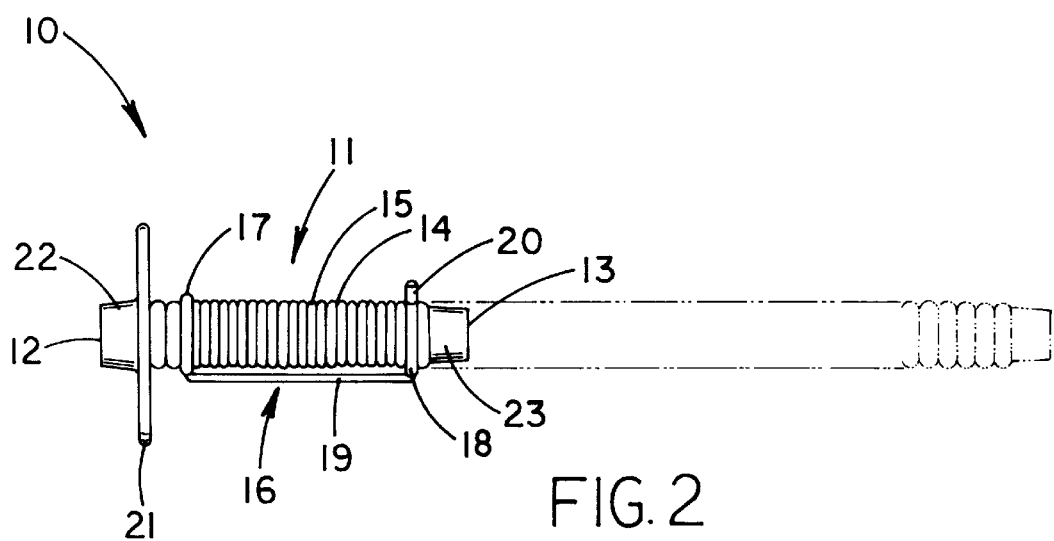
FIG. 2 is a schematic side view of the present invention in the retracted position with the extended position illustrated in phantom lines.
Figure 3:
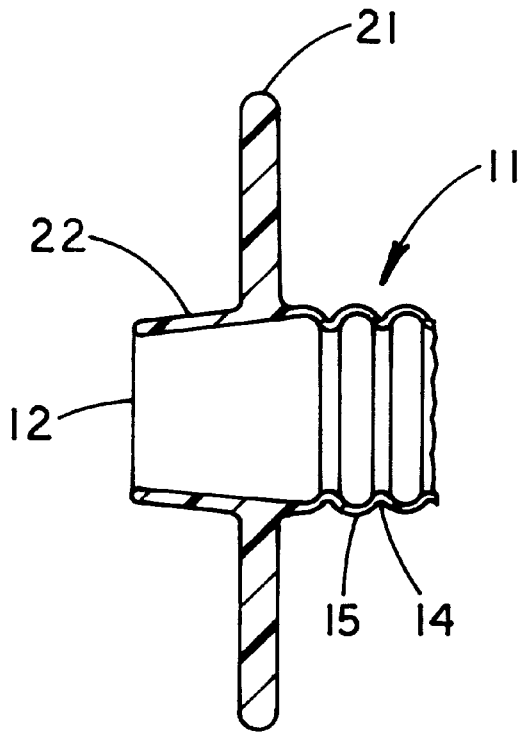
FIG. 3 is a schematic enlarged cross sectional view of the first end region of the present invention.
Figure 4:
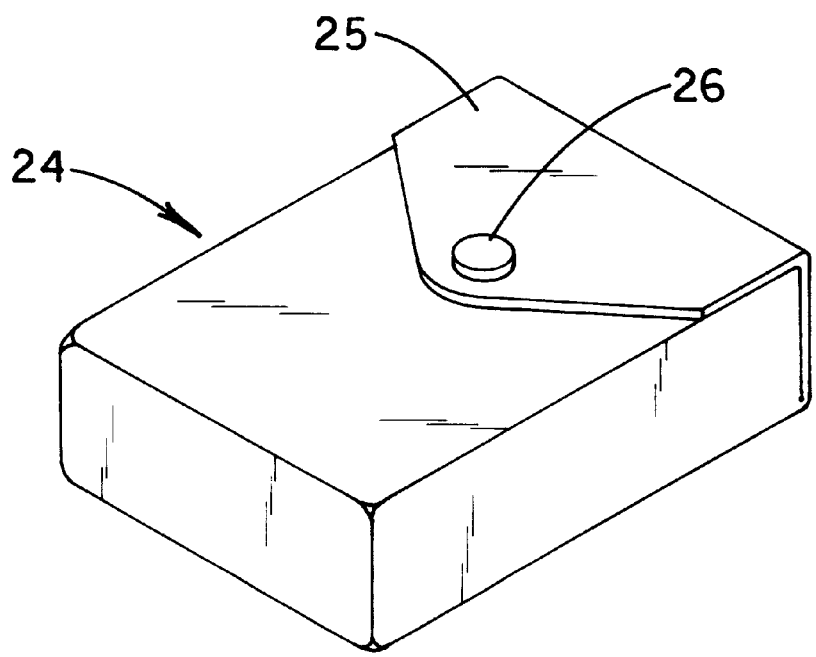
FIG. 4 is a schematic perspective view of a pouch for holding the present invention when in the retracted position.

As best illustrated in FIGS. 1 and 2, the pleats permit retractable extension of the tube in a directional along the longitudinal axis of the tube between a retracted position (FIG. 2) for compact and convenient storage and transport of the aid and an extended position (FIG. 1) for properly optimally using the aid. The tube has a length defined between the ends of the tube. The length of the tube when in the extended position is greater than the length of the tube when in the retracted position. Preferably, the length of the tube when in the extended position is at least about three times greater than the length of the tube when in the retracted position.

A retainer 16 is preferably coupled to the tube to releasably hold the tube in the retracted position. The retainer has a ring 17, a generally C-shaped resilient clip 18, and an elongate flexible portion 19 connecting the ring and clip of the retainer together. The retainer preferably comprises a resilient material such as a resilient rubber or plaster material. The ring of the retainer is disposed around the tube at one of the constricted portions of the tube located towards one of the ends of the tube. As best illustrated in FIG. 2, the clip of the retainer is disposed about tube at another of the constricted portions of the tube located towards the other end of the tube when the tube is in the restricted position such that elongate flexible portion of the retainer is stretched taut between the ring and clip to hold the tube in the retracted position until the clip is removed from about the tube. Preferably, the clip has a pair of opposing ends each with a outwardly flaring tab 20 extending therefrom for aiding insertion of the tube into the clip between the ends to dispose the clip about the tube.

A disk-shaped shield 21 outwardly radiates about the tube and is located towards and spaced apart a first end 12 of the pair ends of the tube.

In use, the first end of the tube is designed for inserted into the vagina of a female user adjacent the opening of the urethra of the user so that urine flowing from the urethra flows into the tube via the first end of the tube and out of the tube via a second end 13 of the pair ends of the tube. The shield is designed for providing a located for a user to place their fingers to hold the first end of the tube in position adjacent the user's urethra and to help prevent urine from accidentally getting on the hands of the user. The pleats permitting bending of the tube into a various positions to permit selective positioning of the ends of the tube with respect to one another so that the second end may be positioned wherever the user so desires to direct the flow of urine from the aid towards a urinal or toilet bowl.

The tube preferably has a pair of tapered regions 22,23 with one of the tapered regions 22 extending between the shield and the first end of the tube and the other tapered region 23 located adjacent the second end of the tube. Each of the tapered regions tapers in a direction towards the adjacent associated end of the tube. The tapered of the first end of the tube is designed for aiding comfortable insertion of the first end of the tube into the user's vagina. The tapered region of the second end of the tube is designed for functioning as a type of nozzle for helping direct the flow of urine therefrom with minimal dripping of urine from the second end.

Optionally, a generally rectangular pouch 24 may be provided for carrying the aid 10 when in a retracted position. The pouch has a flexible flap 25 substantially covering a top opening into the pouch with a fastener 26 such as a snap fastener or a hook and loop fastener detachably attaching the flap to the pouch when the flap covers the top opening of the pouch.

In an ideal illustrative embodiment, the length of the tube when in the extended position is between about 6 inches and about 12 inches to permit adequate extension of the tube away from the user when in use to prevent urine from spraying on to the user from the second end of the tube. In this ideal embodiment, the length of the tube when in the retracted position is preferably about 2 inches to fit in an relatively unobtrusive sized pouch.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A female urinating aid, comprising:
   an elongate tube having a pair of opposite open ends, and a longitudinal axis extending between said ends of said tube;
   wherein said tube comprises a bendable corrugated tube having a series of alternating annular constricted and bellowed portions forming a plurality of annular pleats extending in a row extending between said ends of said tube;
   a disk-shaped shield outwardly radiating about said tube located towards and spaced apart from a first end of said tube;
   each of said bellowed portions of said tube having an outermost diameter defined substantially perpendicular to said longitudinal axis of said tube, wherein said outermost diameters of said bellowed portions are about equal to one another so that an outer diameter of the tube defined by said outermost diameters of said bellowed portions is generally constant along said longitudinal axis of said tube between said ends of said tube;
   wherein said pleats permit retractable extension of said tube in a direction along said longitudinal axis of said tube between a retracted position and an extended position, wherein said tube has a length defined between said ends of said tube, wherein said length of said tube when in said extended position is greater than said length of said tube when in said retracted position; and
   a retainer being coupled to said tube to releasably hold said tube in said retracted position.

2. The female urinating aid of claim 1, wherein said length of said tube when in said extended position is at least about three times greater than said length of said tube when in said retracted position.

3. The female urinating aid of claim 1, wherein said length of said tube when in said extended position is between about 6 inches and about 12 inches, wherein said length of said tube when in said retracted position is about 2 inches.

4. The female urinating aid of claim 1, wherein said retainer has a ring, a generally C-shaped resilient clip, and an elongate flexible portion connecting said ring and clip of said retainer together, wherein said ring of said retainer is disposed around said tube at one of said constricted portions of said tube located towards one of said ends of said tube, and wherein said clip of said retainer is disposed about said tube at another of said constricted portions of said tube located towards the other end of said tube when said tube is in said restricted position.

5. The female urinating aid of claim 4, wherein said clip has a pair of opposing ends each having a outwardly flaring tab extending therefrom.

6. The female urinating aid of claim 1, wherein said tube has a pair of tapered regions, one of said tapered regions extending between said shield and said first end of said tube, the other of said tapered regions being located adjacent a second of said ends of said tube, each of said tapered regions tapering in a direction towards the adjacent associated end of said tube.

7. A female urinating aid, comprising:
   an elongate tube having a pair of opposite open ends, and a longitudinal axis extending between said ends of said tube;
   wherein said tube comprises a bendable corrugated tube having a series of alternating annular constricted and bellowed portions forming a plurality of annular pleats extending in a row extending between said ends of said tube;
   each of said bellowed portions of said tube having an outermost diameter defined substantially perpendicular to said longitudinal axis of said tube, wherein said outermost diameters of said bellowed portions are about equal to one another so that an outer diameter of the tube defined by said outermost diameters of said bellowed portions is generally constant along said longitudinal axis of said tube between said ends of said tube;
   said pleats permitting retractable extension of said tube in a directional along said longitudinal axis of said tube between a retracted position and an extended position;
   said tube having a length defined between said ends of said tube;
   wherein said length of said tube when in said extended position is at least about three times greater than said length of said tube when in said retracted position;
   a retainer being coupled to said tube to releasably hold said tube in said retracted position;
   said retainer having a ring, a generally C-shaped resilient clip, and an elongate flexible portion connecting said ring and clip of said retainer together;
   said ring of said retainer being disposed around said tube at one of said constricted portions of said tube located towards one of said ends of said tube, said clip of said retainer being disposed about said tube at another of said constricted portions of said tube located towards the other end of said tube when said tube is in said restricted position;
   said clip having a pair of opposing ends each having a outwardly flaring tab extending therefrom;
   a disk-shaped shield outwardly radiating about said tube located towards and spaced apart from a first end of said tube; and
   said tube having a pair of tapered regions, one of said tapered regions extending between said shield and said first end of said tube, the other of said tapered regions being located adjacent a second of said ends of said tube, each of said tapered regions tapering in a direction towards the adjacent associated end of said tube.

* * * * *